(12) United States Patent
Lehtiö et al.

(10) Patent No.: US 11,096,909 B2
(45) Date of Patent: Aug. 24, 2021

(54) COMPOUNDS FOR USE IN THE TREATMENT OF CANCER

(71) Applicant: University of Oulu, University of Oulu (FI)

(72) Inventors: Lari Lehtiö, Oulu (FI); Harikanth Venkannagari, Oulu (FI); Bernhard Lüscher, Oulu (FI); Patricia Verheugd, Oulu (FI)

(73) Assignee: University of Oulu, University of Oulu (FI)

( * ) Notice: Subject to any disclaimer, the term of this patent is extended or adjusted under 35 U.S.C. 154(b) by 0 days.

(21) Appl. No.: 16/091,551

(22) PCT Filed: Apr. 6, 2017

(86) PCT No.: PCT/FI2017/050247
§ 371 (c)(1),
(2) Date: Oct. 5, 2018

(87) PCT Pub. No.: WO2017/174879
PCT Pub. Date: Oct. 12, 2017

(65) Prior Publication Data
US 2019/0105289 A1    Apr. 11, 2019

(30) Foreign Application Priority Data

Apr. 6, 2016 (FI) ...................................... 20165300

(51) Int. Cl.
| | | |
|---|---|---|
| *A61K 31/166* | (2006.01) | |
| *C07D 213/30* | (2006.01) | |
| *C07D 239/88* | (2006.01) | |
| *C07C 235/46* | (2006.01) | |
| *C12Q 1/48* | (2006.01) | |
| *A61P 35/00* | (2006.01) | |
| *A61K 45/06* | (2006.01) | |

(52) U.S. Cl.
CPC ............ *A61K 31/166* (2013.01); *A61K 45/06* (2013.01); *A61P 35/00* (2018.01); *C07C 235/46* (2013.01); *C07D 213/30* (2013.01); *C07D 239/88* (2013.01); *C12Q 1/48* (2013.01); *C07C 2601/02* (2017.05); *G01N 2333/91142* (2013.01); *G01N 2500/04* (2013.01)

(58) Field of Classification Search
CPC .................................................. A61K 31/166
See application file for complete search history.

(56) References Cited

U.S. PATENT DOCUMENTS

| 3,983,164 A | 9/1976 | Thorne et al. |
| 8,860,257 B2 | 10/2014 | Schiefermueller et al. |

FOREIGN PATENT DOCUMENTS

| CN | 104163772 A | 11/2014 | |
| EP | 1500643 A1 | 1/2005 | |
| EP | 2414126 A2 | 2/2012 | |
| GB | 1437781 A | 6/1976 | |
| WO | WO-2007012421 A1 * | 2/2007 | ........... C07D 401/12 |
| WO | WO2007012421 A1 | 2/2007 | |
| WO | WO2008024139 A2 | 2/2008 | |
| WO | WO2008030883 A2 | 3/2008 | |
| WO | WO2010100475 A1 | 9/2010 | |
| WO | WO2011017142 A1 | 2/2011 | |
| WO | WO-2017075394 A1 * | 5/2017 | ........... C07D 471/10 |

OTHER PUBLICATIONS

Venkannagari, H., et al. "Small-Molecule Chemical Probe Rescues Cells from Mono-ADP-Ribosyltransferase ARTD10/PARP10-Induced Apoptosis and Sensitizes Cancer Cells to DNA Damage." Cell Chemical Biology. (2016), vol. 23, pp. 1251-1260. (Year: 2016).*
Lehtio, Lari., et al. "Small-Molecule Chemical Probe Rescues Cells from Mono-ADP-Ribosyltransferase ARTD10/PARP10-Induced Apoptosis and Sensitizes Cancer Cells to DNA Damage." Cell Chemical Biology. (2016). vol. 23, pp. 1251-1260. (Year: 2016).*
Ame et al: The PARP superfamily. Bioessays, 2004, vol. 26.8, pp. 882-893.
Andersson et al: Discovery of ligands for ADP-ribosyltransferases via docking-based virtual screening. J Med Chem, Sep. 13, 2012, vol. 55, No. 17, pp. 7706-7718.
Banasik et al: Inhibitors and activators of ADP-ribosylation reactions. Molecular and Cellular Biochemi, Norwell. Jan. 1, 1994, vol. 138, No. 1/02, pp. 185-197.
Barbarulo et al: Poly(ADP-ribose) polymerase family member 14 (PARP14) is a novel effector of the JNK2-dependent pro-survival signal in multiple myeloma. Univ of Leeds, 2013, pp. 4231-4242.
Bell et al: Crystal structure of diphtheria toxin bound to nicotinamide adenine dinucleotide. Biochemistry, Jan. 30, 1996, vol. 35, No. 4, pp. 1137-1149.
Bütepage et al: Intracellular Mono-ADP-Ribosylation in Signaling and Disease. Cells, 2015, vol. 4, pp. 569-595.
Cuzzocrea: Shock, inflammation and PARP. Pharmacol Res., Jul. 2005, vol. 52, No. 1, pp. 72-82.
Ekblad et al: Towards small molecule inhibitors of mono-ADP-ribosyltransferases. European Journal of Medicinal Chemistry, 2015, vol. 95, pp. 546-551.
Feijs et al: ARTD10 substrate identification on protein microarrays: regulation of GSK3ß by mono-ADP-ribosylation. Cell Communication Signaling, 2013, vol. 11, No. 5, pp. 1-11.
Feijs et al: Expanding functions of intracellular resident mono-ADP-ribosylation in cell physiology. The FEBS Journal, 2013, vol. 280, pp. 3519-3529.

(Continued)

*Primary Examiner* — John S Kenyon
(74) *Attorney, Agent, or Firm* — Laine IP Oy

(57) ABSTRACT

It is an aim of the present invention to provide inhibitors of human diphtheria toxin-like ADP-ribosyltransferases, such as ARTD10, for use as a medicine. It is another aim of the invention to provide compounds for use as human mono-ADP-ribosyltransferase (mARTD) inhibitors in vitro. In the present invention, it has been discovered that human ARTD10, which belongs to an enzyme family linked to cancer biology, can be specifically inhibited by the benzamide comprising compounds disclosed in the invention, such as 4,4'-oxydibenzamide.

16 Claims, 7 Drawing Sheets

(56) References Cited

OTHER PUBLICATIONS

Haikarainen et al: Evaluation and Structural Basis for the Inhibition of Tankyrases by PARP Inhibitors. ACS Medicinal Chemistry Letters, 2014, vol. 5, pp. 18-22.
Herzog et al: Caspase-dependent cleavage of the mono-ADP-ribosyltransferase ARTD10 interferes with its pro-apoptotic function. The FEBS Journal, 2013, vol. 280, pp. 1330-1343.
Hottiger et al: ward a unified nomenclature for mammalian ADP-ribosyltransferases. Trends Biochem Sci., Apr. 2010, vol. 35, No. 4, pp. 208-219.
Jones et al: Development and validation of a genetic algorithm for flexible docking. J Mol Biol, Apr. 4, 1997, vol. 267, No. 3, pp. 727-748.
Jwa et al: PARP16 is a tail-anchored endoplasmic reticulum protein required for the PERK and IRE1a-mediated unfolded protein response. Nat Cell Biol, Nov. 2012, vol. 14, No. 11, pp. 1223-1230.
Kleine et al: Substrate-Assisted Catalysis by PARP10 Limits Its Activity to Mono-ADP-Ribosylation. Molecular Cell, Oct. 10, 2008, vol. 32, pp. 57-69.
Koc et al: Hydroxyurea Arrests DNA Replication by a Mechanism That Preserves Basal dNTP Pools*. The J of Biological Chemistry, 2004, vol. 279, No. 1, pp. 223-230.
Lord et al: Synthetic lethality and cancer therapy: lessons learned from the development of PARP inhibitors. Annu Rev Med., 2015, vol. 66, pp. 455-470.
Marona et al: Preliminary evaluation of anticonvulsant activity of some 4-(benzyloxy)-benzamides. Acta Poloniae Pharmaceutica, 2003, vol. 60, No. 6, pp. 477-480.
Morgan et al: Selective inhibition of PARP10 using a chemical genetics strategy. Bioorg Med Chem Lett, Nov. 1, 2015, vol. 25, No. 21, pp. 4770-4773.
Narwal et al: Homogeneous Screening Assay for Human Tankyrase. J of Biomolecular Screening, 2012, vol. 17, No. 5, pp. 593-604.
Nicolae et al: A novel role for the mono-ADP-ribosyltransferase PARP14/ARTD8 in promoting homologous recombination and protecting against replication stress. Nucleic Acids Research, 2015, vol. 43, No. 6, pp. 3143-3153.
Nicolae et al: The ADP-ribosyltransferase PARP10/ARTD10 Interacts with Proliferating Cell Nuclear Antigen (PCNA) and Is Required for DNA Damage Tolerance. The Journal of Biological Chem, May 9, 2014, vol. 19, pp. 13627-13637.
Otto et al: In silico characterization of the family of PARP-like poly(ADP-ribosyl)transferases (pARTs). BMC Genomics, 2005, vol. 6, No. 139, pp. 1471-2164.
Ruf et al: The mechanism of the elongation and branching reaction of poly(ADP-ribose) polymerase as derived from crystal structures and mutagenesis. J Mol Biol, Apr. 24, 1998, vol. 278, No. 1, pp. 57-65.
Scarpa et al: A role of intracellular mono-ADP-ribosylation in cancer biology. The FEBS Journal, 2013, vol. 280, pp. 3551-3562.
Wahlberg et al: Family-wide chemical profiling and structural analysis of PARP and tankyrase inhibitors. Nat Biotechnol, Feb. 19, 2012, vol. 30, No. 3, pp. 283-288.
Waszkielewicz et al: Synthesis and preliminary evaluation of anticonvulsant activity of some [4-(benzyloxy) benzoyl]- and [4-(benzyloxy) benzyl]aminoalkanol derivatives. Acta Poloniae Pharmaceutica, 2007, vol. 64, No. 2, pp. 147-157.
Venkannagari et al: Activity-based assay for human mono-ADP-ribosyltransferases ARTD7/PARP15 and ARTD10/PARP10 aimed at screening and profiling inhibitors. European Journal of Pharmaceutical Sciences, Feb. 26, 2013, vol. 49, pp. 148-156.
Verheugd et al: Regulation of NF-kB signalling by the mono-ADP-ribosyltransferase ARTD10. Nature Communications, Apr. 9, 2013, vol. 4:1683, pp. 1-11.
Virag et al: Poly(ADP-ribosyl)ation in asthma and other lung diseases. Pharmacol Res, Jul. 2005, vol. 52, No. 1, pp. 83-92.
Vyas et al: New PARP targets for cancer therapy. Nat Rev Cancer, Jul. 2014, vol. 14, No. 7, pp. 502-509.
Yu et al: PARP-10, a novel Myc-interacting protein with poly(ADP-ribose) polymerase activity, inhibits transformation. Oncogene, 2005, vol. 24, pp. 1982-1993.
Raffa et al: Synthesis, antiproliferative activity and possible mechanism of action of novel 2-acetamidobenzamides bearing the 2-phenoxy functionality. Bioorganic & Medicinal Chemistry, Aug. 28, 2015, vol. 23, No. 19, pp. 6305-6316.

* cited by examiner

OULL-0128
1012 nM

OULL-0086
228 nM

OULL-0085
831 nM

OULL-0105
515 nM

OULL-0110
134 nM

OULL-0132
1177 nM

OULL-0133
645 nM

OULL-0111
2067 nM

OULL-0129
4068 nM

COMPOUNDS FOR USE IN THE TREATMENT OF CANCER

TECHNICAL FIELD

The present invention relates to the field of enzyme inhibitors useful for cancer treatments. Particularly, the present invention provides inhibitors of human diphtheria toxin-like ADP-ribosyltransferase 10 (ARTD10/PARP10). ARTD enzymes are ADP-ribosyltransferases having various activities in cellular signaling, DNA repair, apoptosis and cell proliferation. In particular, ARTD10 is a mono-ADP-ribosyltransferase. The benzamide comprising compounds disclosed in the present invention are small molecule inhibitors suitable for use as a medicine and in the treatment of cancers such as hematopoietic cancers, osteosarcoma, breast carcinoma, liver cancer, pancreatic cancer, pancreatic glioma and pancreatic carcinoid.

BACKGROUND OF THE INVENTION

The human diphtheria toxin-like ADP-ribosyltransferase (ARTD or PARP) family includes 17 members that share a conserved catalytic domain responsible for ADP-ribosylation of substrate proteins[1-3]. While some ARTDs modify substrates by transferring iteratively multiple ADP-ribose units resulting in poly-ADP-ribosylation (PARylation), most ARTDs mono-ADP-ribosylate (MARylate) their substrates[4].

PARylating ARTDs (pARTDs; ARTD1-6), most prominently ARTD1/PARP1, have been the focus of cancer related research during the past two decades. The ARTD1 inhibitor olaparib (Lynparza) has been approved to treat ovarian cancer with BRCA mutations[30]. However, olaparib as well as several other ARTD1 inhibitors are not specific[11], which indicates that further studies are required to evaluate the contribution of different ARTDs to the phenotypes observed. This is relevant because recent studies have linked MARylating ARTDs (mARTDs) to cancer biology[12]. Notably, ARTD10/PARP10 has been suggested to be a potential drug target in cancer[5].

MARylation, a covalent reversible post-translational modification of proteins, is associated with various cellular processes[13,14]. ARTD10 was first identified as a binding partner of the oncoprotein c-Myc and it was the first member of the ARTD family to be fully characterized as an mARTD[4]. ARTD10 has a conserved C-terminal ART domain responsible for its enzymatic activity[2-4,15]. In vitro screening of more than 8000 proteins identified 78 substrates for ARTD10[10], the majority of these being kinases. ADP-ribosylation of GSK3-β by ARTD10 negatively regulates the kinase activity of GSK3-β in vitro and knockdown of ARTD10 increased the kinase activity of GSK3-β in cells[10].

Other prior art relating to PARP inhibitors are:
WO2015051766 disclosing amide substituted indazoles and benzotriazoles which are inhibitors of the enzyme poly (ADP-ribose) polymerase (PARP). Said amide substituted indazoles and benzotriazoles were disclosed to be useful as mono-therapies in tumors with specific defects in DNA-repair pathways;
WO2014201972 disclosing benzimidazole-2-piperazine heterocyclic derivative and pharmaceutical composition comprising the same, and use of the derivative as a therapeutic agent, particularly as a poly (ADP-ribose) polymerase (PARP) inhibitor; and
U.S. Pat. No. 8,993,594 disclosing substituted isoquinolin-1(2H)-one derivatives which selectively inhibit the activity of poly (ADP-ribose) polymerase PARP-1 with respect to poly (ADP-ribose) polymerase PARP-2. The compounds were disclosed to be useful in treating diseases such as cancer, cardiovascular diseases, central nervous system injury and different forms of inflammation.

Further, U.S. Pat. No. 8,980,902 and US2015031652 disclose compounds that may be used to inhibit PARP.

EP1500643 discloses benzamide derivatives inhibiting Rho kinase. The authors disclose that morbidity due to diseases such as hypertension and cancers is expected to be improved by inhibition of the Rho kinase and the $Na^+/H^+$ exchange transport system. It is also disclosed that cancers are improved by the effect of Rho kinase inhibitors on cell overproliferation. Examples of EP1500643 specifically disclose 4-(piperidin-4-yloxy)benzamide trifluoroacetate and 5-chloro-2-methoxy-4-(piperidin-4-yloxy)benzamide as potential Rho kinase inhibitors.

Growing interest in the development of ARTD inhibitors culminated in the recent approval of the ARTD1-4 inhibitor Olaparib (Lynparza) for the treatment of ovarian cancer[30]. The less studied members of the superfamily, mARTDs, have recently attracted attention as potential new drug targets[11,22-24]. It is clear that the existing ARTD inhibitors are not selective and, although they inhibit certain mARTDs, they cannot be used to evaluate the cellular effects of inhibiting these enzymes[11]. Intracellular MARylation plays multiple roles in cancer biology as it is involved in cellular signaling events including stress and immune responses[5,9,14,25]. Hence there is a need to identify new more specific inhibitors to be used as research tools and to evaluate mARTDs as potential drug targets.

SUMMARY OF THE INVENTION

It is an aim of the present invention to provide inhibitors of human ARTD10 for use as a medicine.

It is another aim of the invention to provide compounds for use as human mono ADP-ribosyltransferase (mARTD) inhibitors in vitro.

In the present invention, it has been discovered that human ARTD10, which belongs to an enzyme family linked to cancer biology, can be specifically inhibited by the compounds disclosed in the invention.

Thus, in one aspect the invention provides a compound having a general formula

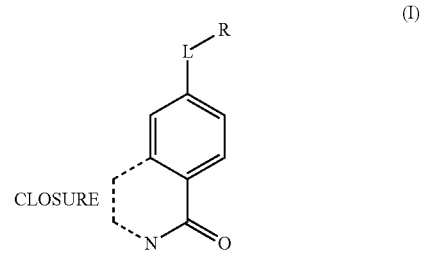

wherein:
the CLOSURE structure provides part of a 5-7-membered unsaturated or saturated heterocyclic group or alternatively the CLOSURE structure is absent, wherein the CLOSURE structure is replaced by hydrogen atoms H and/or $H_2$;

L represents a linker of 1, 2, 3 or 4 linking atom(s) in a linear or in a branched conformation, and being selected from the group consisting of: C, O, N or S, wherein at least one of the linking atoms is oxygen (O);

R is a saturated or unsaturated $C_{1-6}$ alkyl, saturated or unsaturated cycloalkyl, saturated or unsaturated heteroalkyl or a saturated or unsaturated heterocyclic ring system consisting of 1 or 2 heterocyclic rings, wherein said alkyl, cycloalkyl, heteroalkyl or ring system may contain at least one substituent selected from a group consisting of: H, F, Cl, Br, I, $C_{1-3}$ alkyl, halogen-substituted $C_{1-3}$ alkyl, $C_{1-3}$ alkoxy, halogen-substituted $C_{1-3}$ alkoxy, —CN, —OH, —COOH, —CONH$_2$ and —NO$_2$, and wherein L is O, R is not piperidin-4-yl or piperidin-4-yl with a Cl-substituent; or a tautomer, stereoisomer or a pharmaceutically acceptable salt thereof; for use as a medicine.

In another aspect, the invention provides a pharmaceutical composition comprising a human ARTD10 inhibitor as defined in the invention and a pharmaceutically acceptable carrier, excipient, or stabilizer.

In another aspect, the invention provides a use of a human ARTD10 inhibitor as defined in the invention for the manufacture of a medicament.

In another aspect, the invention provides a method of treating cancer comprising a step of administering a human ARTD10 inhibitor as defined in the invention to a patient suffering from a cancer.

In another aspect, the invention provides a method of treating inflammatory disorder comprising a step of administering a human ARTD10 inhibitor as defined in the invention to a patient suffering from an inflammatory disorder.

In another aspect, the invention provides a use of a human ARTD10 inhibitor as defined in the invention as a mono ADP-ribosyltransferase (mARTD) inhibitor in vitro.

DESCRIPTION OF EMBODIMENTS

Figure 1:
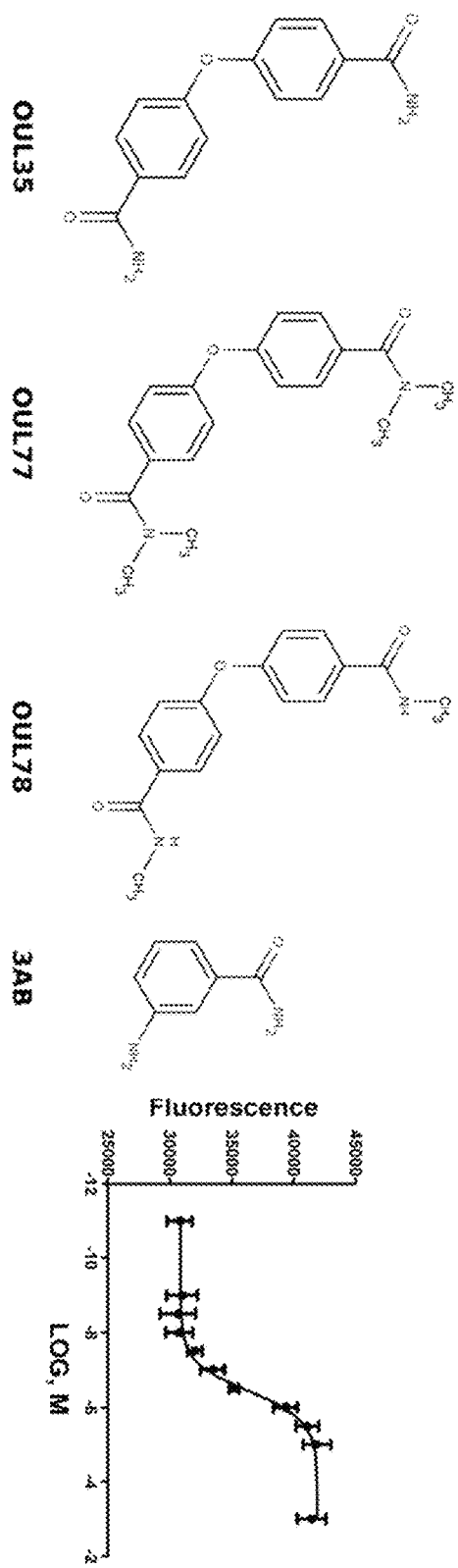
FIG. 1. Chemical structures of OUL35; inactive analogs OUL77 and OUL78; general ARTD inhibitor 3AB; and a dose-response curve for OUL35 against ARTD10.

ADP-ribosylation of proteins by human diphtheria toxin-like ADP-ribosyltransferase 10 (ARTD10) plays important roles in various activities ranging from cellular signaling, DNA repair and cell proliferation to the immune response. Here we describe small molecule ARTD10 inhibitors, the first reported selective and potent inhibitors for this enzyme and so far the only selective inhibitors of any of the mono-ADP-ribosyltransferases in the ARTD family. We show in the Experimental Section below that these compounds can be selective among the homologous ARTD enzyme family, rescue HeLa cells from ARTD10 induced cell death and also sensitize the cells to hydroxyurea induced DNA damage.

The present invention is thus directed to a compound having a general formula

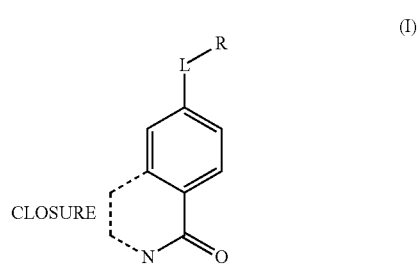

(I)

wherein:

the CLOSURE structure provides part of a 5-7-membered unsaturated or saturated heterocyclic group or alternatively the CLOSURE structure is absent, wherein the CLOSURE structure is replaced by hydrogen atoms H and/or H$_2$;

L represents a linker of 1, 2, 3 or 4, preferably 1 or 2, linking atom(s) in a linear or in a branched conformation, and being selected from the group consisting of: C, O, N or S, wherein at least one of the linking atoms is oxygen (O);

R is a saturated or unsaturated $C_{h6}$ alkyl, saturated or unsaturated cycloalkyl preferably consisting of 1 or 2 monocyclic rings, saturated or unsaturated heteroalkyl or a saturated or unsaturated heterocyclic ring system consisting of 1 or 2 heterocyclic rings, wherein said alkyl, cycloalkyl, heteroalkyl or ring system may contain at least one substituent, preferably 1-2 or 1-3 substituents, selected from a group consisting of: H, F, Cl, Br, I, $C_{1-3}$ alkyl, halogen-substituted $C_{1-3}$ alkyl, $C_{1-3}$ alkoxy, halogen-substituted $C_{1-3}$ alkoxy, —CN, —OH, —COOH, —CONH$_2$ and —NO$_2$, and wherein L is O, R is not piperidin-4-yl or piperidin-4-yl with a Cl-substituent;

or a tautomer, stereoisomer or a pharmaceutically acceptable salt thereof;

for use as a medicine.

Preferably, said compound has a general formula

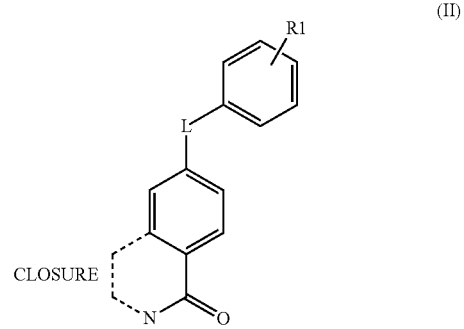

(II)

wherein:

the CLOSURE structure provides part of a 5-7-membered unsaturated or saturated heterocyclic group or alternatively the CLOSURE structure is absent, wherein the CLOSURE structure is replaced by hydrogen atoms H and/or $H_2$;

L represents a linker of 1, 2, 3 or 4 linking atom(s) in a linear or in a branched conformation, said atom(s) being selected from the group consisting of: C, O, N or S wherein at least one of the linking atoms is oxygen (O);

R1 is on 2, 3 or 4 position of the phenyl group and is selected from the group consisting of: H, F, Cl, Br, I, $C_{1-3}$ alkyl, halogen-substituted $C_{1-3}$ alkyl, $C_{1-3}$ alkoxy, halogen-substituted $C_{1-3}$ alkoxy, —CN, —OH, —COOH, —$CONH_2$ and —$NO_2$.

More preferably, R1 is $CONH_2$ or a halogen such as F. Linker L is preferably 0 or C.

In an embodiment, the CLOSURE structure comprises 1, 2 or 3 carbon atoms, such as structures CH, $C_2H_2$ or $C_3H_3$. In an embodiment, wherein the CLOSURE structure is absent, the chain of carbon atoms of a heterocyclic group is replaced by hydrogen atoms H and/or $H_2$.

In the embodiments of the invention, linker L is preferably selected from the group consisting of: O, NH, N(—$CH_3$), C(=O), O—$CH_2$, O—C(=O), C(=O)—O, and O—$CH_2$—$CH_2$—O.

Accordingly, in linker L the linking atoms can have substituents such as H or $H_2$ or branched structures such as $CH_3$, or =O.

Preferably, said compound is 4,4'-oxydibenzamide having the formula

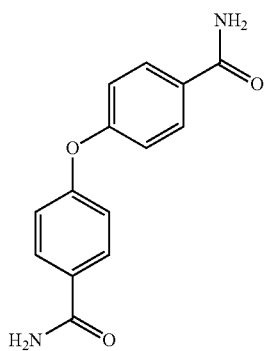

(III)

wherein L is O; R1 is —$CONH_2$ on 4 position of the phenyl group and the CLOSURE structure is absent.

In another preferred embodiment, the said compound has a general formula:

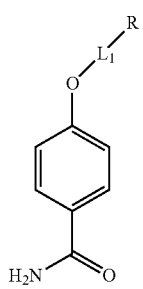

(Ib)

wherein R is as defined above and $L_1$ is absent or an extended linker structure selected from a group consisting of: C(=O), $CH_2$, CH(—CH3) and $CH_2$—$CH_2$—O. Preferably, $L_1$ is selected from a group consisting of: C(=O) or $CH_2$.

In another embodiment, the compound preferably has the formula

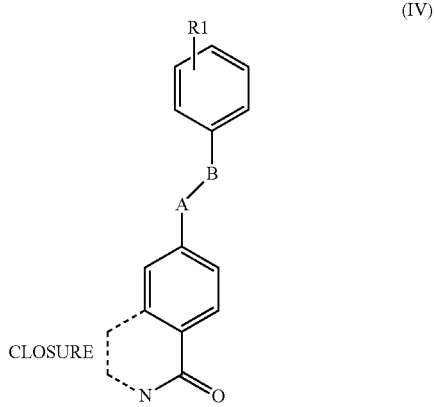

(IV)

wherein L contains linking atoms A and B. R1 and the CLOSURE structure are as defined above. Linking atoms A and B are selected from the group consisting of: C, O, N or S, wherein at least A or B is oxygen (O). Preferably, the A is oxygen (O) and B is carbon (C), wherein the linker has the structure O—$CH_2$. Other preferred linkers are $CH_2$—O, O—C(=O) or C(=O)—O.

More preferably, said compound has the formula

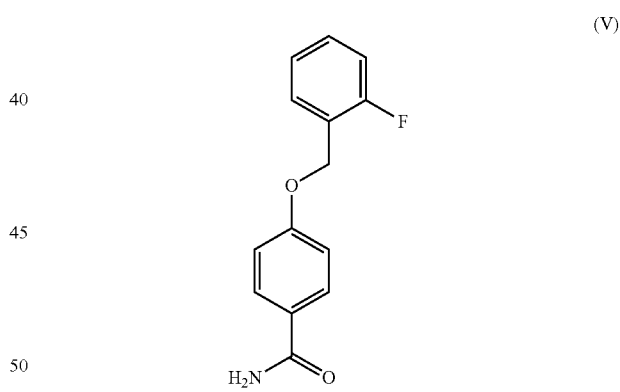

(V)

wherein the linker L contains linking atoms oxygen (O) as atom A and carbon (C) as atom B, i.e. the linker is O—$CH_2$, and R1 is fluorine (F) on 2 position of the phenyl group and the CLOSURE structure is not present.

As used herein, "alkyl" is intended to include both branched and straight-chain saturated aliphatic hydrocarbon groups having the specified number of carbon atoms. For example, "$C_{1-3}$ alkyl" is defined to include groups having 1, 2, or 3 carbons in a linear or branched arrangement. Preferred alkyl groups are methyl (—$CH_3$) and ethyl (—$CH_2CH_3$).

As used herein "halogen-substituted" refers to structures where one or more hydrogen atoms have been replaced by halogen atoms. The term "halogen" refers to fluorine, chlorine, bromine and iodine.

The term "alkoxy" represents an alkyl group of indicated number of carbon atoms attached through an oxygen bridge. An example of suitable alkoxy groups is $C_{1-3}$ alkoxy which includes methoxy, ethoxy and propoxy.

The compounds as defined in Formulas I-V may have asymmetric or chiral structures and thus occur as racemates, racemic mixtures, or as individual diastereomers, or with all possible isomers and mixtures thereof, including optical isomers, all such stereoisomers being in the scope of this description. In addition, the compounds disclosed herein may exist as tautomers and both tautomeric forms are intended to be encompassed by the scope of this description, even though only one tautomeric structure is depicted.

Preferably, the present compounds are for use in the treatment of cancer. The effect of the present compounds is expected to be larger in cancers where ARTD10 mRNA and subsequently proteins levels are higher than normal cells. Based on this, the preferred applications would be in the treatment of hematopoietic cancers including leukemias and lymphomas, osteosarcoma, breast carcinoma, liver cancer, pancreatic cancer, pancreatic glioma and pancreatic carcinoid.

Other cancers treatable by the present compounds are carcinomas such as bladder, colon, kidney, lung, including small cell lung cancer, esophagus, gall-bladder, ovary, stomach, cervix, thyroid, prostate, and skin carcinoma, including squamous cell carcinoma; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, xeroderma pigmentosum, keratoxanthoma, thyroid follicular cancer and Kaposi's sarcoma.

The results also indicate that the present compounds could be used as a general agent to enhance the effect of DNA damaging drugs causing stalling of the replication fork. Therefore, the present compounds are preferably used together with a chemotherapeutic agent such as a DNA damaging compound and/or with radiotherapy. Preferred DNA-damaging anticancer compounds are platinum-based compounds, such as cisplatin, carboplatin, oxaliplatin, and picoplatin, and anthracyclines such as doxorubicin and daunorubicin and also methotrexate. Other preferred DNA-damaging anticancer compounds are topoisomerase I inhibitors such as irinotecan, topotecan, camptothecin and lamellarin D.

Accordingly, the present compounds are useful in combination with anti-cancer agents or chemotherapeutic agents. The compounds of Formula I may be useful as chemo- and radio-sensitizers for cancer treatment. They are useful for the treatment of patients who have previously undergone or are presently undergoing treatment for cancer. Such previous treatments include prior chemotherapy, radiotherapy, surgery or immunotherapy.

PARP inhibitors have been demonstrated as being useful for treatment of inflammatory disorders[28,29], therefore the present compounds are also for use in the treatment of inflammatory disorders such as acne vulgaris, asthma, autoimmune diseases, autoinflammatory diseases, celiac disease, chronic prostatitis, glomerulonephritis, hypersensitivities, inflammatory bowel diseases, pelvic inflammatory disease, reperfusion injury, rheumatoid arthritis, sarcoidosis, transplant rejection, vasculitis, and interstitial cystitis.

Treatable patients in this invention include mammalian patients, preferably human patients. This is supported by the fact that the catalytic domain of ARTD10 is conserved in mammals. Catalytic domains of ARTD10 for chimpanzee and human are 99.1% similar. In rhesus macaque (monkey), the similarity is 94.1%. In Guinea pig, the similarity is 75%, but still all the active site residues in the catalytic domain that contribute to the inhibitor binding are conserved. Likewise, the bovine catalytic domain is 74% identical to human and the corresponding homology in sheep is 72.7%.

In an embodiment, the present invention also relates to pharmaceutical compositions which contain an inhibitor of the Formula I-V or a pharmaceutically acceptable salt thereof as active ingredient. These pharmaceutical compositions are for example those for enteral, such as in particular oral, those for parenteral administration, and those for local administration to a patient.

The pharmaceutical compositions according to the invention usually contain the pharmacologically active ingredient according to Formula I-V together with known pharmaceutically acceptable carriers, excipients, diluents, adjuvants, fillers, buffers, stabilisers, preservatives or lubricants. The amount of the active ingredient in the pharmaceutical compositions according to the invention is, for example, from about 0.001% to 100% by weight, preferably from about 0.1% to about 50% by weight. The dose of the active ingredient can depend on various factors, such as the efficacy of the active ingredient, severity of the disease to be treated or its symptoms, administration procedure, sex, age, weight and/or individual condition of the subject in need of the treatment. In a normal case, for a human adult of about 75 kg in weight, one daily dose of about 1 mg to about 1000 mg, in particular from about 10 mg to about 500 mg, is to be estimated. This can be administered as a single dose or in several sub-doses.

In an embodiment, the pharmaceutical compositions may be in the form of an injectable aqueous solution. The injectable preparation may also be an injectable oil-in-water microemulsion where the active ingredient is dissolved in the oily phase. The injectable solutions or microemulsions may be introduced into a patient's blood stream by local bolus injection. The pharmaceutical compositions may be in the form of a sterile injectable aqueous or oleagenous suspension for intramuscular and subcutaneous administration. This suspension may be formulated according to the known art using suitable dispersing or wetting agents and suspending agents.

The preparation of typical pharmaceutically acceptable salts is described by Berge et al. (1977) *J. Pharm. Sci.* "Pharmaceutical Salts", 66: 1-19.

In an embodiment, the present invention is also directed to the use of the compound as defined by Formula I, Ib, II, III, IV or V for the manufacture of a medicament, preferably for the treatment of cancer or inflammatory disorders. Advantageously, said compound is used together with a chemotherapeutic agent and/or with radiotherapy as described above.

In an embodiment, the present invention is directed to a method of treating cancer or inflammatory disorder comprising a step of administering the compound as defined by Formula I, Ib, II, III, IV or V to a patient suffering from a cancer or inflammatory disorder.

The present invention also provides a use of the compound as defined by Formula I, Ib, II, III, IV or V as a mono ADP-ribosyltransferase (mARTD) inhibitor in vitro, preferably as an ARTD10 inhibitor in vitro. The present invention is thus directed to an in vitro method comprising a step contacting the compound as defined by Formula I, Ib, II, III, IV or V with a sample suspected or known to comprise mARTDs, preferably ARTD10, in order to inhibit activity of the mARTDs in the sample. Preferably, said method comprises a further step of contacting said compound with a control sample comprising a mono ADP-ribosyltransferase (mARTD) such as ARTD10.

In an further embodiment, the present invention is also directed to an in vitro screening method for identifying inhibitors of a mono ADP-ribosyltransferase (mARTD), preferably ARTD 10, comprising:

a) contacting a candidate compound having a general formula

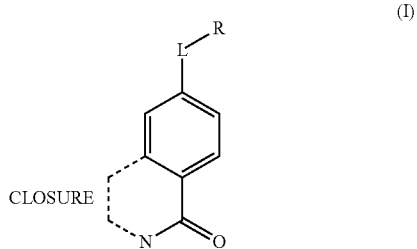

(I)

wherein:

the CLOSURE structure provides part of a 5-7-membered unsaturated or saturated heterocyclic group or alternatively the CLOSURE structure is absent, wherein the CLOSURE structure is replaced by hydrogen atoms H and/or $H_2$;

L represents a linker of 1, 2, 3, or 4, preferably 1 or 2, linking atom(s) in a linear or in a branched conformation, said atom(s) being selected from the group consisting of: C, O, N or S;

R is a saturated or unsaturated $C_{h6}$ alkyl, saturated or unsaturated cycloalkyl preferably consisting of 1 or 2 monocyclic rings, saturated or unsaturated heteroalkyl or a saturated or unsaturated heterocyclic ring system consisting of 1 or 2 heterocyclic rings, wherein said alkyl, cycloalkyl, heteroalkyl or ring system may contain at least one substituent selected from a group consisting of: H, F, Cl, Br, I, $C_{1-3}$ alkyl, halogen-substituted $C_{1-3}$ alkyl, $C_{1-3}$ alkoxy, halogen-substituted $C_{1-3}$ alkoxy, —CN, —OH, —COOH, —CONH$_2$ and —NO$_2$;

or a tautomer, stereoisomer or a pharmaceutically acceptable salt thereof;

with a mono ADP-ribosyltransferase;

b) measuring the level of enzymatic activity of the mono ADP-ribosyltransferase in the presence of said candidate compound;

c) selecting those candidate compounds which inhibit the mono ADP-ribosyltransferase.

Preferably, the candidate compound selected in step c) can rescue cells overexpressing said mono ADP-ribosyltransferase. the candidate compound selected in step c) is tested to be a selective inhibitor of said mono ADP-ribosyltransferase.

Having now generally described the invention, the same will be more readily understood by reference to the following Experimental Section, which is provided by way of illustration and is not intended as limiting.

Although methods and materials similar or equivalent to those described herein can be used in the practice or testing of the present invention, suitable methods and materials are described below.

EXPERIMENTAL SECTION

Example 1

Used Proteins

All the proteins used in the study were produced recombinantly in E. coli host. Details for the amino acid composition of each construct are described in Tables 1 and 2. Proteins were purified using affinity chromatography (Ni-NTA) and size-exclusion chromatography. DNA binding ARTDs were further purified on a heparin column before performing the size-exclusion chromatography. In some cases the 6× his-tag was cleaved from the fusion proteins (ARTD12, ARTD15). The protocol described above summarizes the general purification method followed for all the proteins used in this study. More details about constructs used in different assays are given in Tables 1 and 2.

Differential Scanning Fluorimetry

Differential scanning fluorimetry was performed with protein concentrations of 0.25 mg/ml. Details of the expression constructs used for each ARTD are provided in Table 1. The concentration of OUL35 was 100 μM. Control wells without the compound contained an equal amount of the DMSO vehicle as the melting curves in the presence of OUL35. Sypro Orange (Life Technologies) was used as the reporter dye with a final concentration of 20×. The experiment was performed on a real time PCR machine (Applied Biosystems) with the temperature increasing from 21° C. up to 90° C. (70 cycles) with 1 degree increment per minute.

TABLE 1

Details of the constructs used for performing thermal stability assay.

| ARTD | Amino Acid composition |
|---|---|
| ARTD1 | 654-1013 |
| ARTD2 | 234-579 |
| ARTD3 | 176-532 |
| ARTD4 | 250-565 |
| ARTD5 | 1091-1325 |
| ARTD6 | 952-1161 |
| ARTD7 | 460-656 |
| ARTD8 | 1611-1801 |
| ARTD10 | 809-1017 |
| ARTD10 (G888W) | 809-1017 |
| ARTD10 (L926Y) | 809-1017 |
| ARTD10 (R931A) | 809-1017 |
| ARTD12 | 489-684 |
| ARTD13 | 726-896 |
| ARTD15 | 1-280 |

Activity Assays

Screening of the compound libraries against ARTD10 was performed based on our previously validated activity-based fluorescent assay[6]. Profiling and dose response experiments were conducted as described previously[6,18]. As detailed in our earlier publication[16] some of the mARTDs are very sensitive to increasing concentrations of DMSO. In these cases we tested a maximum concentration of 10 μM for compound OUL35. Details of the assay conditions and expression constructs used for each ARTD are provided in Table 2.

TABLE 2

Constructs and conditions used in the activity assays.

| ARTD | Amino Acids | Assay Conditions |
|---|---|---|
| ARTD1 | 1-1014 | 5 nM ARTD1 and NAD$^+$ 500 nM 50 mM Tris pH 8, 2 mM Mg$^{2+}$, 10 μg/mL activated DNA 1.5 h shaking at RT |

TABLE 2-continued

Constructs and conditions used in the activity assays.

| ARTD | Amino Acids | Assay Conditions |
|---|---|---|
| ARTD2 | 1-583 | 5 nM ARTD2 and NAD+ 500 nM 50 mM Tris pH 8, 5 mM Mg$^{2+}$, 10 µg/mL activated DNA 1.5 h shaking at RT |
| ARTD3 | 1-533 | 200 nM ARTD3 and 500 nM NAD+ 50 mM HEPES pH 7, 10 µg/mL DNA, 8 mM MgCl2 3 h shaking at RT |
| ARTD4 | 250-565 | 200 nM ARTD4 and 500 nM NAD+ 50 mM Na—P buffer pH 7.5, 0.5 mM TCEP, 1 mg/mL BSA 2.5 h shaking at RT |
| ARTD5 | 1030-1317 | 20 nM ARTD5 and 500 nM NAD+ 50 mM BisTris propane pH 7, 0.5 mM TCEP, 0.01% Triton X-100 18 h shaking at RT |
| ARTD6 | 873-1161 | 20 nM ARTD6 and 500 nM NAD+ 50 mM BisTris propane pH 7, 0.5 mM TCEP, 18 h shaking at RT/300 rpm |
| ARTD7 | 460-656 | 200 nM ARTD7, 500 nM SRPK2 and 250 nM NAD+ 50 mM Na—P pH 7 8 h shaking at RT |
| ARTD8 | 1535-1801 | 500 nM ARTD8 and 250 nM NAD+ 50 mM Na—P pH 7.0 21 h shaking at RT |
| ARTD 10 | 809-1017 | 100 nM ARTD10, 2 µM SRPK2 and 500 nM NAD+ 50 mM Tris pH 7.0 13 h shaking at RT |
| ARTD 12 | 489-701 | 500 nM ARTD12 and 500 nM NAD+ 50 mM Na—P pH 7 20 h shaking at RT |
| ARTD 15 | 1-280 | 2 µM ARTD 15 and 500 nM NAD+ 50 mM HEPES ph 7, 2 mM NiCl2 24 h shaking at RT |

Docking of OUL35

GOLD[27] was used to analyze the binding mode of OUL35 to the catalytic domain of ARTD10. The available ARTD10 crystal structure (3HKV) contains mutations, but they are located outside the expected binding pocket and do not contribute to the binding of OUL35. The binding pocket was defined with an 8 Å radius based on the nicotinamide mimicking 3AB present in the crystal structure. Hydrogen atoms were added, ligands and water molecules removed, and the program defaults were used with the ChemPLP scoring function. The top three binding poses produced by the genetic algorithm were essentially the same indicating a likely solution in the docking experiment.

Colony Formation Assay

Three hundred HeLa cells designed to express the wild-type ARTD10 and catalytically inactive ARTD10 (G888W) in response to doxycycline were seeded in 6 cm well culture plates. The cells were grown in DMEM culture media with 10% FCS, and the plates were incubated at 37° C. with 5% CO$_2$. After 24 h of seeding, over expression of ARTD10 was induced by adding 500 ng/ml doxycycline and the media were also supplemented with the tested compounds at 10 µM concentrations. The cells were allowed to proliferate for the next 10 days, after which they were stained with methylene blue to count the number of surviving colonies. The compounds and doxycycline were replenished every 48 h while fresh media (DMEM supplemented with 10% FCS) was added every four days.

DNA Damage Experiments

HeLa cells (ATCC) were grown in Dulbecco's modified Eagle's medium (DMEM, Sigma) supplemented with 10% fetal bovine serum (Lonza), 1× penicillin and streptomycin (Sigma) at 37° C. in a 5% CO2 atmosphere. 4000 cells/well were plated on 96-well plates. The cells were allowed to attach for 6 hours before treatment with hydroxyurea combined with 5 µM OUL35 or DMSO vehicle in serum free medium. The DMSO content was kept below 0.05% in all experiments. The 96-well plates were placed in an IncuCyte ZOOM live cell imaging system (Essen BioScience) to follow the cell growth. The plates were scanned in the IncuCyte at 2 hour intervals for 72 hours. Data were analyzed by the IncuCyte Zoom software (Essen BioScience). The results are representative of three (cell growth curves) or five independent experiments (72 h end points) each done in six replicates. P values less than 0.05 were considered as significant (n.s=not statistically significant, *P<0.05, **P<0.01).

Results

Discovery of a Potent and Selective ARTD10 Inhibitor

Earlier we described a robust activity-based assay for ARTD10, which was validated for screening of compound libraries[16]. Here we applied this assay for the screening of compound libraries from the open chemical repository of the National Cancer Institute (NCI). Dose response measurements of the hit compound revealed OUL35 (4,4'-oxydibenzamide), which had an IC$_{50}$ value of 329 nM (FIG. 1). Treatment of HeLa cells with 10 µM of OUL35 showed that OUL35 has no cytotoxic effect.

Profiling and Selectivity

There are 17 ARTD enzymes in the human ARTD superfamily, which all contain a homologous catalytic domain. Therefore it was essential to verify the selectivity of OUL35 for ARTD10. The non-selectivity of the "PARP inhibitors" is a known issue and some efforts have recently been devoted to understanding the inhibitor profile[11,17]. We used our established assay method[16,18] to profile the selectivity of OUL35 against the ARTDs available in our laboratory (Table 3). Profiling experiments revealed that OUL35, despite its small molecular weight and simple structure, was highly selective towards ARTD10 over the other enzymes of the family (Table 3). OUL35 also inhibited ARTD8 (23.4 µM), ARTD4 (22.6 µM), and ARTD15 (4.17 µM) but with modest potency (Table 3). Selectivity was further validated by differential scanning fluorimetry (DSF) to test for binding of the compound. This activity independent method also allowed us to include inactive ARTD13 in the profiling. DSF verified binding of OUL35 to the ARTD10 catalytic domain and its selectivity over other ARTDs. OUL35 stabilized the catalytic domains of ARTD10, ARTD8 & ARTD15 as expected based on the enzymatic assays (Table 3).

TABLE 3

IC$_{50}$ and thermal stabilization of OUL35 against a panel of human ARTD enzymes.

| ARTD/PARP | IC50 (pIC50 ± SEM) | ΔTm (DSF), ° C. ± STDEV |
|---|---|---|
| ARTD1/PARP1 | >100 µM | 0.42 ± 0.09 |
| ARTD2/PARP2 | >100 µM | 0.15 ± 0.12 |
| ARTD3/PARP3 | >100 µM | 0.09 ± 0.32 |
| ARTD4/PARP4 | 22.6 µM (4.65 ± 0.17) | 0.84 ± 0.14 |
| ARTD5/PARP5a | >100 µM | 0.45 ± 0.01 |
| ARTD6/PARP5b | >100 µM | 0.15 ± 0.12 |
| ARTD7/PARP15 | >20 µM$^a$ | 1.19 ± 0.10 |
| ARTD8/PARP14 | 23.4 µM (4.63 ± 0.09) | 3.00 ± 0.21 |
| ARTD10/PARP10 | 329 nM (6.48 ± 0.04) | 3.76 ± 0.10 |

TABLE 3-continued

IC$_{50}$ and thermal stabilization of OUL35
against a panel of human ARTD enzymes.

| ARTD/PARP | IC50 (pIC50 ± SEM) | ΔTm (DSF), ° C. ± STDEV |
|---|---|---|
| ARTD12/PARP12 | >100 µM | 0.87 ± 0.42 |
| ARTD13/PARP13 | ND | −0.21 ± 0.04 |
| ARTD15/PARP16 | 4.17 µM (5.38 ± 0.06) | 2.45 ± 0.11 |

[a]Compound concentration limited by ARTD DMSO sensitivity. Less than 50% inhibition was observed when tested at 20 µM concentration.

OUL35 contains a nicotinamide mimicking motif like most of the ARTD inhibitors reported to date[11] (FIG. 1). It consists of two symmetrical benzamide motifs that could compete with the binding of NAD$^+$ in the nicotinamide binding site. Based on this hypothesis we designed two small modifications to the compound yielding OUL77 and OUL78, which we expected to be inactive and useful as control compounds when evaluating OUL35 in biological systems (FIG. 1). Neither of the methylated analogs at concentrations of 1 µM or 10 µM inhibited ARTD10 supporting our results. Based on the biochemical and biophysical analysis OUL35 is a potentially useful tool to study ARTD10 functions in cells.

Modelling

Figure 2:
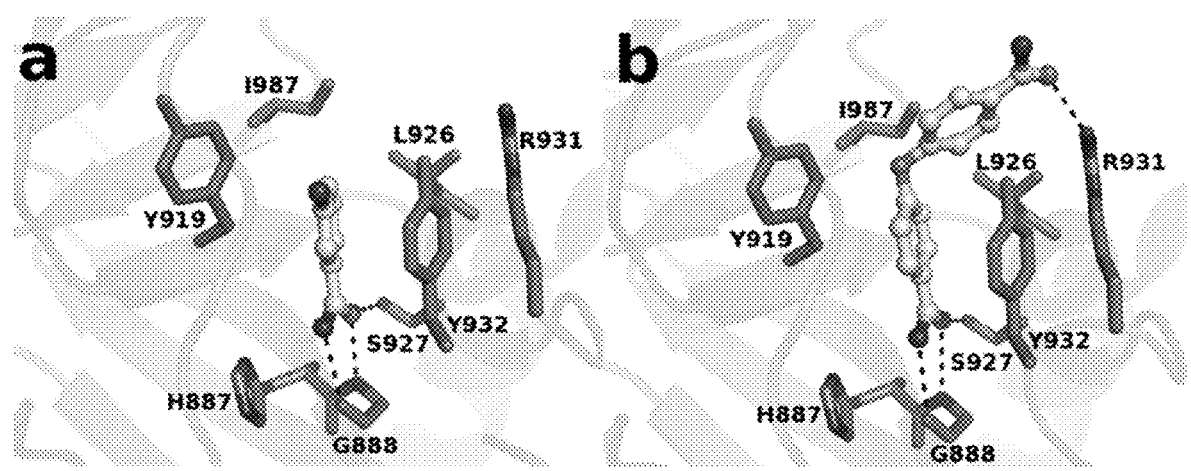
FIG. 2. Comparison of the docking pose with the crystal structure of ARTD10 (a) 3-aminobenzamide (3AB) in complex with ARTD10 (PDB id. 3HKV) (b) Docking pose of OUL35 with ARTD10. OUL35 is expected to bind to the nicotinamide site in a similar manner to 3AB.

To understand the structural basis for inhibition and selectivity of OUL35 against ARTD10 we performed docking studies using the available crystal structure of an ARTD10 mutant (PDB id. 3HKV). There are no NAD$^+$ complex structures with ARTDs available and our understanding of the substrate binding is based on the NAD$^+$ binding mode in the diphtheria toxin[19] (PDB id. 1TOX) and on NAD$^+$ mimicking inhibitors[17]. The crystal structure of ARTD10 contains a small general ARTD inhibitor 3-aminobenzamide (3AB), which binds to the nicotinamide binding site of ARTDs (FIG. 1). The chemical structure of OUL35 suggests that the benzamide moiety would bind to the nicotinamide pocket in a manner similar to the nicotinamide of the substrate NAD$^+$ and the small general ARTD inhibitor 3AB (FIG. 1). Based on this assumption, we expect that OUL35 extends from the pocket towards the acceptor site where the ADP-ribosylation target protein binds. The acceptor site is deduced from the NAD$^+$ analog found partially visible in the chicken ARTD1 structure[20]. Docking studies revealed that the best binding pose indeed overlaps with 3AB found in the co-crystal structure and that OUL35 extends towards the acceptor site (FIG. 2).

OUL35 Rescues HeLa Cells from ARTD10-Induced Cell Death

Figure 3:
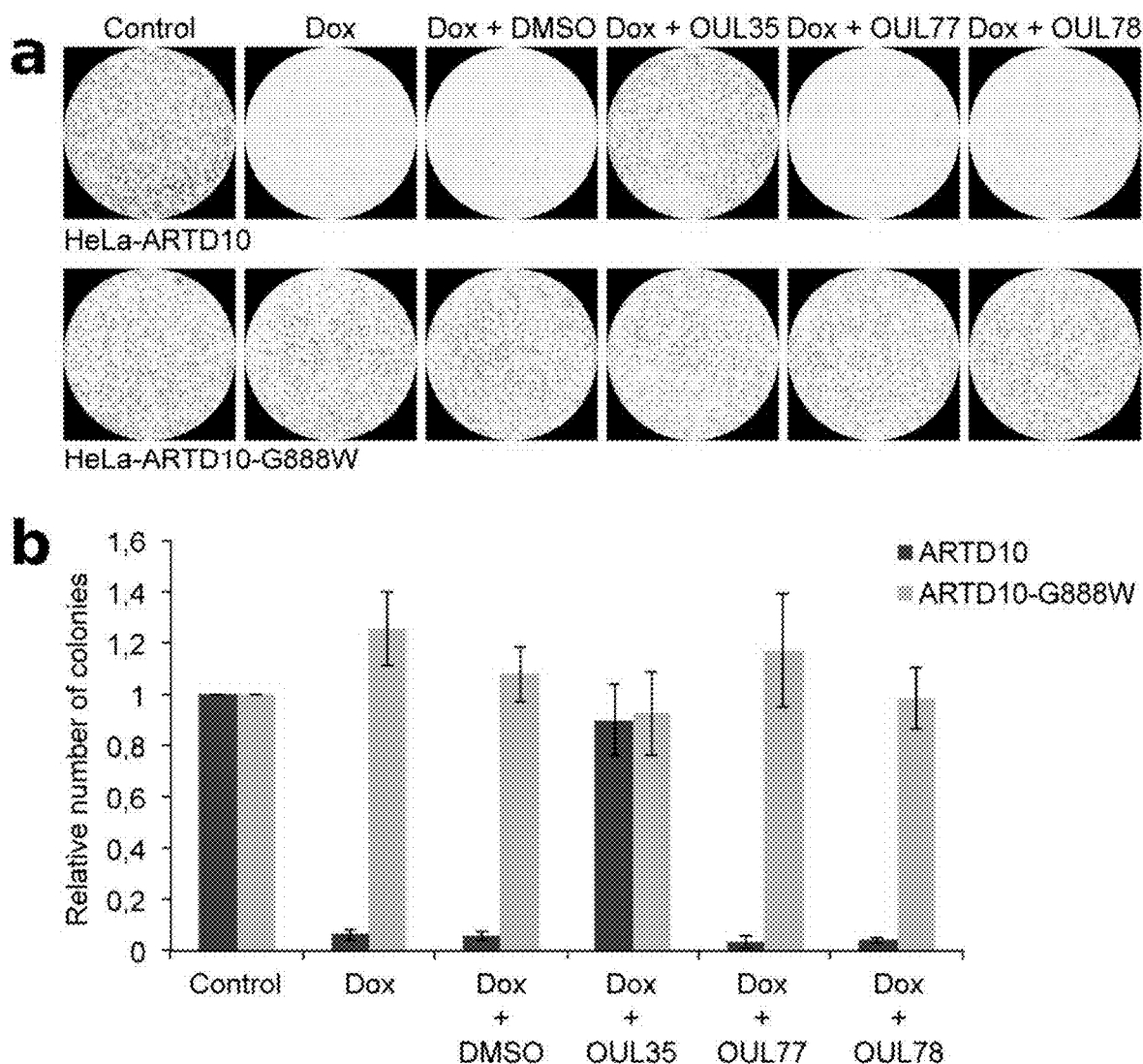
FIG. 3. OUL35 rescues ARTD10 overexpressing cells (a) Images of the wells from colony formation experiments. ARTD10 expression was not induced in cells in the control wells, while the expressions of ARTD10 and the inactive mutant ARTD10-GW (G888W) were induced with doxycycline (Dox, 500 ng/ml) in the rest of the wells. The different compounds were added as indicated with a final concentration of 10 μM. These were replenished every 48 h. (b) Quantification of the colony formation results. The data represent mean values of three independent experiments performed in duplicates with standard deviations.

Over-expression of wild-type ARTD10 but not the catalytically inactive mutant ARTD10-G888W leads to cell death[8]. Colony formation assays were performed to assess whether OUL35 can enter cells and inhibit endogenous ARTD10 and whether the toxic effect of ARTD10 could be rescued by inhibiting its ADP-ribosylation activity. As expected, overexpression of wild-type ARTD10 but not ARTD10-G888W strongly inhibited cell proliferation (FIG. 3a, b). The treatment of HeLa cells overexpressing ARTD10 with OUL35 resulted in a complete rescue of cell proliferation. Notably the inactive analogs OUL77 and OUL78 were ineffective and did not facilitate colony formation (FIG. 3). Moreover none of the compounds showed any toxicity in the control cells. Together these findings provide evidence that OUL35 is taken up by cells and inhibits the catalytic activity of ARTD10.

Figure 4:
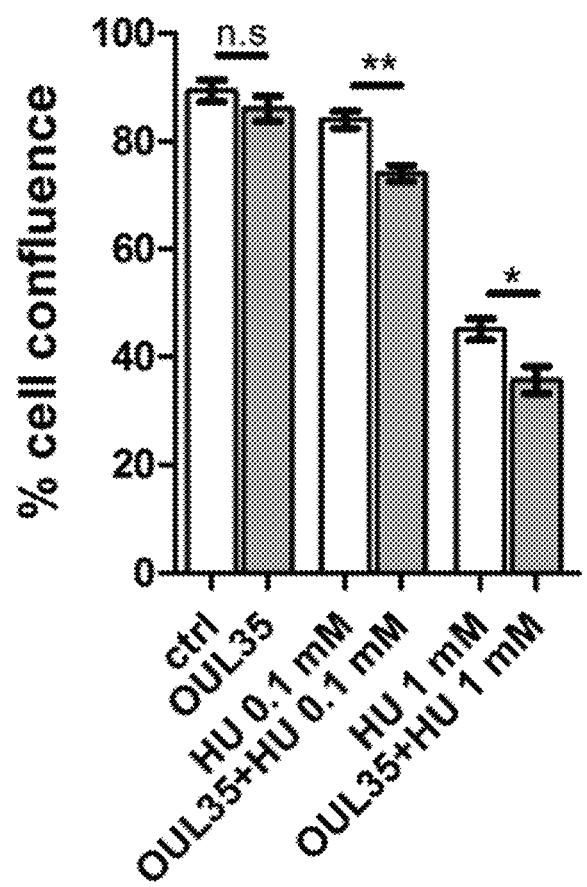
FIG. 4. The effect of OUL35 on HeLa cells treated with hydroxyurea. Cell confluence is indicated at 72 hours (n=5, data present mean±SEM, n.s=not significant, *P<0.05, **P<0.01).

Hydroxyurea Sensitivity Confirms the Role of ARTD10 in Genotoxic Stress Response Hydroxyurea (HU) inhibits ribonucleotide reductase and thus interferes with deoxyribonucleotide synthesis. This results in inhibition of S phase and causes stalled replication forks[21]. ARTD10 knockdown cells are more sensitive to HU-induced DNA damage as the catalytic activity is necessary for its DNA repair functions[5]. We investigated whether we could reproduce this effect by inhibiting the enzymatic activity of ARTD10 in HeLa cells. HeLa cells treated with HU were more sensitive to DNA damage in the presence of OUL35 (FIG. 4). Thus using a specific chemical probe we confirmed that the enzymatic activity of ARTD10 is indeed required for the recovery of the cells from the hydroxyurea induced genotoxic stress.

DISCUSSION

Here, the small molecule OUL35 was identified as a selective inhibitor of one of the mARTDs—ARTD10. The compound is able to enter cultured cells and inhibit ARTD10-dependent cellular processes. Structural analysis suggested the basis of the selectivity over the other ARTD enzymes and the docking model indicated that OUL35 would be the first ARTD/PARP inhibitor extending towards the acceptor site. While OUL35 is selective towards ARTD10 it can also be used in the design of other mARTD inhibitors due to the structural similarities of the binding sites. Notably, the identified mARTDs that show weak affinity to OUL35 are also suggested to be involved in cancer linked processes. ARTD8 plays a role in the survival of cancerous multiple myeloma cells[26] and promotes DNA damage repair[6], while ARTD15 is a regulator of the unfolded protein response[7].

OUL35 was not toxic to control cells in our experiments, but it efficiently rescued cells overexpressing ARTD10 and reproduced the effects seen by ARTD10 knockdown using RNAi[5,8]. The results provide additional evidence for the role of ARTD10 in S phase DNA damage repair. OUL35 will aid further studies to assess the roles of ARTD10 in different processes.

Example 2

Figure 5:
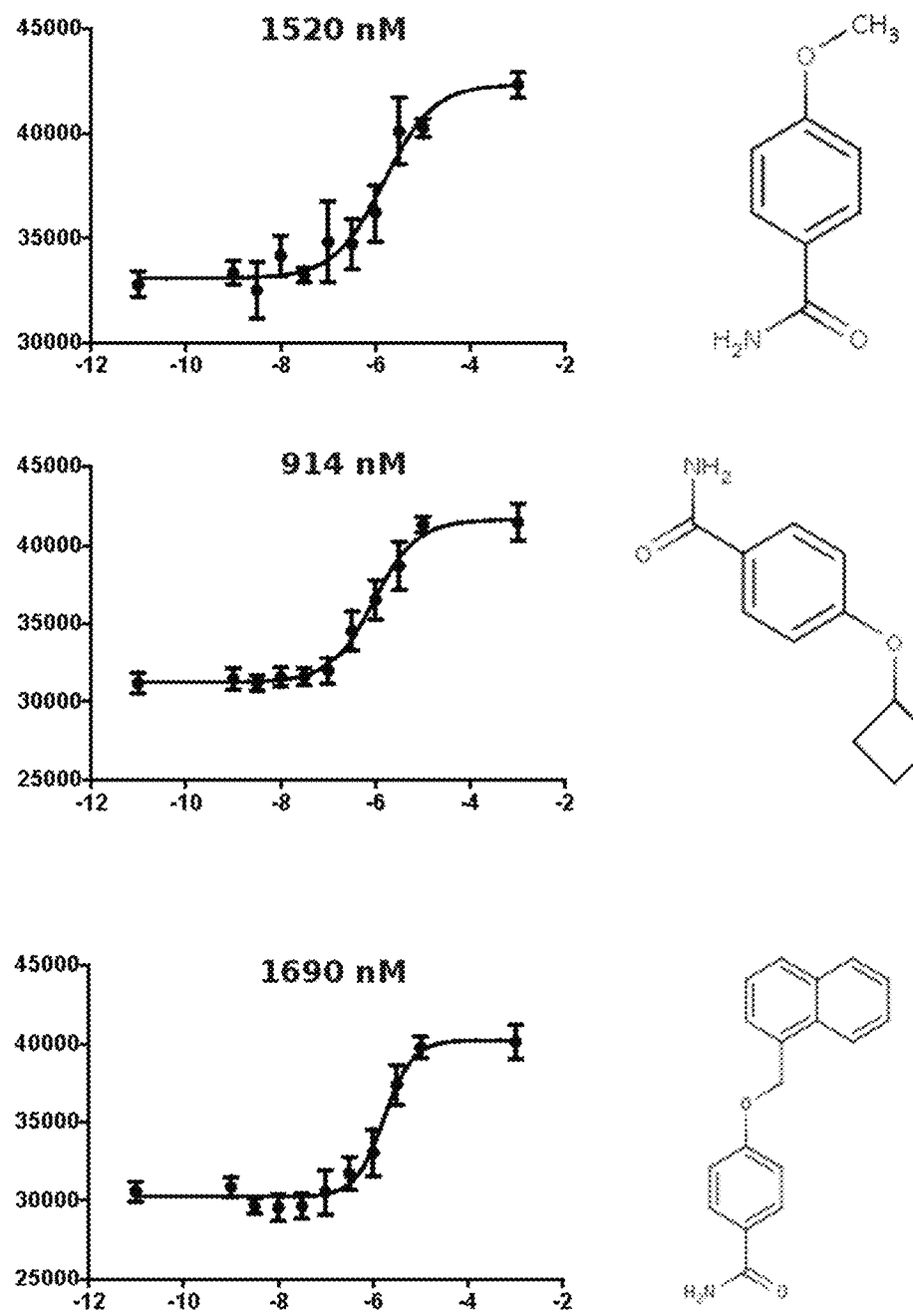
FIG. 5. Dose-response curves for example compounds against ARTD10. On X-axis concentration (LOG, M) and on Y-axis Fluorescence.
Figure 6:
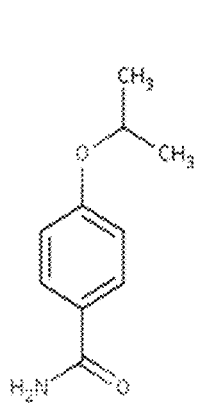
FIG. 6. Examples of structures with an O-linker having inhibiting effect against ARTD10.
Figure 6:
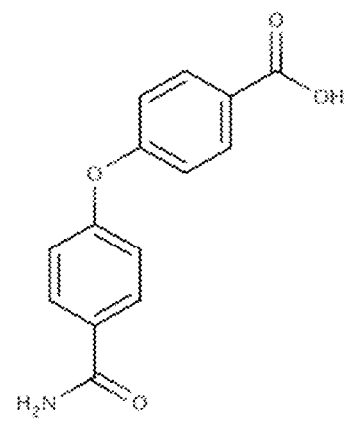
Figure 6:
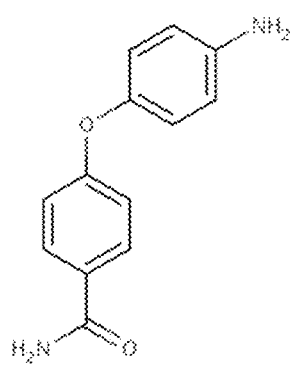
Figure 7:
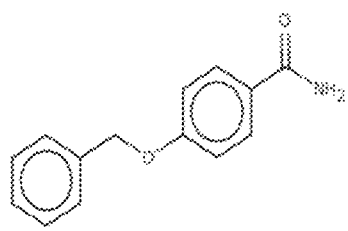
FIG. 7. Examples of structures with a longer O-linker having inhibiting effect against ARTD10.
Figure 7:
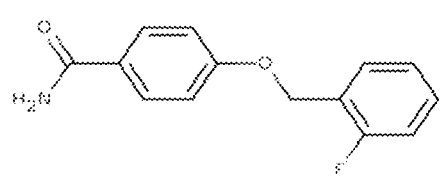
Figure 7:
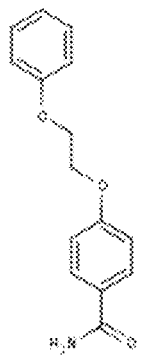
Figure 7:
Figure 7:
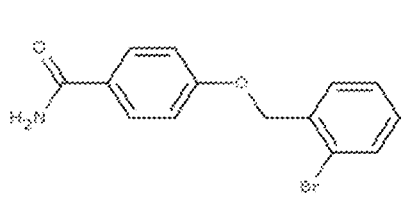
Figure 7:
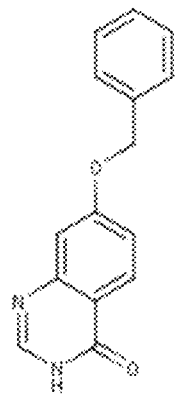

Various R substituents are effective in the scaffold as described in Formula (I). The compounds were assayed for the inhibition of ARTD10 activity as described above and examples of the effective groups in the contexts of the variable linkers are shown in FIGS. 5-7. These results show that the minimum R group in the context of a one atom linker (L) is a methyl group, although the increase of the size improves the potency like in the case of a cyclobutyl. Also a large bulky naphtalenyl group is tolerated as an R group.

REFERENCES

1. Ame, J.-C., Spenlehauer, C. & de Murcia, G. The PARP superfamily. *BioEssays* 26, 882-893 (2004).
2. Otto, H. et al. In silico characterization of the family of PARP-like poly(ADP-ribosyl)transferases (pARTs). BMC Genomics 6,139 (2005).
3. Hottiger, M. O., Hassa, P. O., Lüscher, B., Schüler, H. & Koch-Nolte, F. Toward a unified nomenclature for mammalian ADP-ribosyltransferases. *Trends Biochem. Sci.* 35, 208-219 (2010).

4. Kleine, H. et al. Substrate-Assisted Catalysis by PARP10 Limits Its Activity to Mono-ADP-Ribosylation. *Mol. Cell* 32, 57-69 (2008).
5. Nicolae, C. M. et al. The ADP-ribosyltransferase PARP10/ARTD10 Interacts with Proliferating Cell Nuclear Antigen (PCNA) and Is Required for DNA Damage Tolerance. *J. Biol. Chem.* 289, 13627-13637 (2014).
6. Nicolae, C. M. et al. A novel role for the mono-ADP-ribosyltransferase PARP14/ARTD8 in promoting homologous recombination and protecting against replication stress. *Nucleic Acids Res.* 43, 3143-3153 (2015).
7. Jwa, M. & Chang, P. PARP16 is a tail-anchored endoplasmic reticulum protein required for the PERK- and IRE1α-mediated unfolded protein response. *Nat. Cell Biol.* 14, 1223-1230 (2012).
8. Herzog, N. et al. Caspase-dependent cleavage of the mono-ADP-ribosyltransferase ARTD10 interferes with its pro-apoptotic function. *FEBS J.* 280, 1330-1343 (2013).
9. Verheugd, P. et al. Regulation of NF-idB signalling by the mono-ADP-ribosyltransferase ARTD10. *Nat. Commun.* 4, 1683 (2013).
10. Feijs, K. L. et al. ARTD10 substrate identification on protein microarrays: regulation of GSK3f3 by mono-ADP-ribosylation. *Cell Commun. Signal.* 11, 5 (2013).
11. Wahlberg, E. et al. Family-wide chemical profiling and structural analysis of PARP and tankyrase inhibitors. *Nat. Biotechnol.* 30, 283-288 (2012).
12. Vyas, S. & Chang, P. New PARP targets for cancer therapy. *Nat. Rev. Cancer* 14, 502-509 (2014).
13. Feijs, K. L. H., Verheugd, P. & Lüscher, B. Expanding functions of intracellular resident mono-ADP-ribosylation in cell physiology. *FEBS J.* 280, 3519-3529 (2013).
14. Bütepage, M., Eckei, L., Verheugd, P. & Lüscher, B. Intracellular Mono-ADP-Ribosylation in Signaling and Disease. *Cells* 4, 569-595 (2015).
15. Yu, M. et al. PARP-10, a novel Myc-interacting protein with poly(ADP-ribose) polymerase activity, inhibits transformation. *Oncogene* 24, 1982-1993 (2005).
16. Venkannagari, H., Fallarero, A., Feijs, K. L. H., Lüscher, B. & Lehtiö, L. Activity-based assay for human mono-ADP-ribosyltransferases ARTD7/PARP15 and ARTD10/PARP10 aimed at screening and profiling inhibitors. *Eur. J. Pharm. Sci.* 49, 148-156 (2013).
17. Haikarainen, T., Narwal, M., Joensuu, P. & Lehtiö, L. Evaluation and Structural Basis for the Inhibition of Tankyrases by PARP Inhibitors. *ACS Med. Chem. Lett.* 5, 18-22 (2014).
18. Narwal, M., Fallarero, A., Vuorela, P. & Lehtiö, L. Homogeneous screening assay for human tankyrase. *J. Biomol. Screen.* 17, 593-604 (2012).
19. Bell, C. E. & Eisenberg, D. Crystal structure of diphtheria toxin bound to nicotinamide adenine dinucleotide. *Biochemistry (Mosc.)* 35, 1137-1149 (1996).
20. Ruf, A., Rolli, V., de Murcia, G. & Schulz, G. E. The mechanism of the elongation and branching reaction of poly(ADP-ribose) polymerase as derived from crystal structures and mutagenesis. *J. Mol. Biol.* 278, 57-65 (1998).
21. Koç, A., Wheeler, L. J., Mathews, C. K. & Merrill, G. F. Hydroxyurea Arrests DNA Replication by a Mechanism That Preserves Basal dNTP Pools. *J. Biol. Chem.* 279, 223-230 (2004).
22. Ekblad, T. et al. Towards small molecule inhibitors of mono-ADP-ribosyltransferases. *Eur. J. Med. Chem.* 95, 546-551 (2015).
23. Morgan, R. K., Carter-O'Connell, I. & Cohen, M. S. Selective inhibition of PARP10 using a chemical genetics strategy. *Bioorg. Med. Chem. Lett.* (2015). doi:10.1016/j.bmcl.2015.07.033
24. Andersson, C. D. et al. Discovery of ligands for ADP-ribosyltransferases via docking-based virtual screening. *J. Med. Chem.* 55, 7706-7718 (2012).
25. Scarpa, E. S., Fabrizio, G. & Di Girolamo, M. A role of intracellular mono-ADP-ribosylation in cancer biology. *FEBS J.* 280, 3551-3562 (2013).
26. Barbarulo, A. et al. Poly(ADP-ribose) polymerase family member 14 (PARP14) is a novel effector of the JNK2-dependent pro-survival signal in multiple myeloma. *Oncogene* 32, 4231-4242 (2013).
27. Jones, G., Willett, P., Glen, R. C., Leach, A. R. & Taylor, R. Development and validation of a genetic algorithm for flexible docking. *J. Mol. Biol.* 267, 727-748 (1997).
28. Cuzzocrea, S. Shock, inflammation and PARP. *Pharmacological Research* Volume 52, Issue 1, July 2005, Pages 72-82.
29. Virág, L. Poly(ADP-ribosyl)ation in asthma and other lung diseases. *Pharmacological Research* Volume 52, Issue 1, July 2005, Pages 83-92.
30. Lord C J, Tutt A N, and Ashworth A. Synthetic lethality and cancer therapy: lessons learned from the development of PARP inhibitors. Annu Rev Med. 2015; 66:455-70.

CITED PATENT DOCUMENTS

EP1500643
U.S. Pat. No. 8,993,594
U.S. Pat. No. 8,980,902
US2015031652
WO2015051766
WO2014201972

The invention claimed is:

1. A method of treating cancer or an inflammatory disorder, the method comprising administering to a subject in need thereof a compound having a general formula:

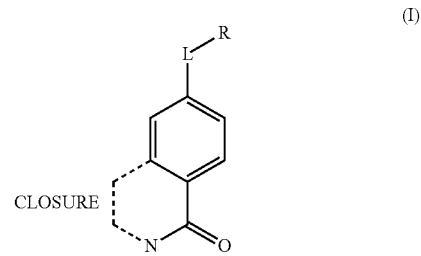

or a tautomer, stereoisomer or a pharmaceutically acceptable salt thereof, wherein:

the CLOSURE structure is absent, and wherein the CLOSURE structure is replaced by a hydrogen atom on a carbon of the phenyl ring and by $H_2$ on the nitrogen atom of Formula(I);

L represents a linker of 1 or 2 linking atom(s) in a linear or in a branched conformation, and being selected from the group consisting of: C, O, N or S, wherein at least one of the linking atoms is oxygen (O);

R is a saturated or unsaturated cycloalkyl or an unsaturated heterocyclic ring system consisting of 1 heterocyclic ring, wherein said cycloalkyl or heterocyclic ring system optionally comprises at least one substituent selected from a group consisting of: H, F, Cl, Br, I, $C_{1-3}$ alkyl, halogen-substituted $C_{1-3}$ alkyl, $C_{1-3}$ alkoxy, halogen-substituted $C_{1-3}$ alkoxy, —CN, —OH, —COOH, —CONH$_2$, and —NO$_2$.

2. The method according to claim 1, the compound having a formula

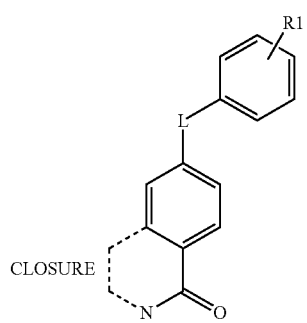

(II)

wherein:
the CLOSURE structure is absent and is replaced by a hydrogen atom on the phenyl ring and by H$_2$ on the nitrogen atom of Formula(II);
L represents a linker of 1 or 2 linking atom(s) in a linear or in a branched conformation, said atom(s) being selected from the group consisting of: C, O, N or S, wherein at least one of the linking atoms is oxygen (O); and
wherein R1 is optionally present on a 2, 3 or 4 position of the phenyl group and is selected from the group consisting of: H, F, Cl, Br, I, $C_{1-3}$ alkyl, halogen-substituted $C_{1-3}$ alkyl, $C_{1-3}$ alkoxy, halogen-substituted $C_{1-3}$ alkoxy, —CN, —OH, —COOH, —CONH$_2$ and NO$_2$.

3. The method according to claim 1, wherein linker L is selected from the group consisting of: O and O—CH$_2$.

4. The method according to claim 2, wherein said compound is 4,4'-oxydibenzamide having the formula:

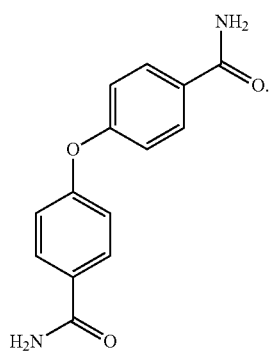

(III)

5. The method according to claim 1, said compound having the formula:

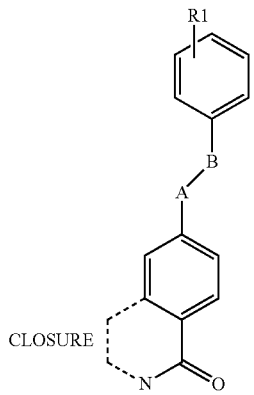

(IV)

wherein R1 is optionally present on a 2, 3 or 4 position of the phenyl group and represents a member selected from the group consisting of: H, F, Cl, Br, I, $C_{1-3}$ alkyl, halogen-substituted $C_{1-3}$ alkyl, $C_{1-3}$ alkoxy, halogen-substituted $C_{1-3}$ alkoxy, —CN, —OH, —COOH, —CONH$_2$ and NO$_2$, and wherein the linker L of Formula (I) contains linking atoms A and B, and wherein A and B together represent linkers selected from O—CH$_2$, CH$_2$—O, O—C(=O) or C(=O)—O.

6. The method according to claim 5, said compound having the formula:

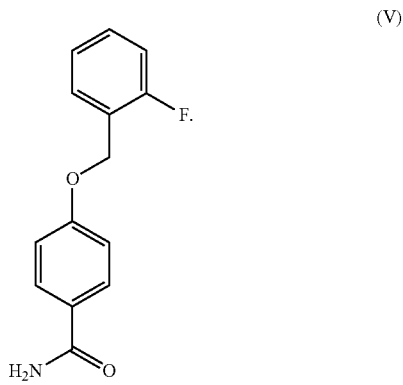 [SMILES: NC(=O)c1ccc(OCc2ccccc2F)cc1]

(V)

7. The method according to claim 1, wherein the compound is administered to the subject in conjunction with chemotherapy and/or radiotherapy.

8. The method according to claim 1, wherein said cancer is selected from the group consisting of: hematopoietic cancers, osteosarcoma, breast carcinoma, liver cancer, pancreatic cancer, glioma, and carcinoid.

9. The method according to claim 7, wherein said chemotherapy is performed with a DNA damaging agent selected from the group consisting of: hydroxyurea, cisplatin, carboplatin, oxaliplatin, picoplatin, doxorubicin, daunorubicin and methotrexate.

10. An in vitro method for the inhibition of mARTDs comprising a step of contacting a compound having a general formula:

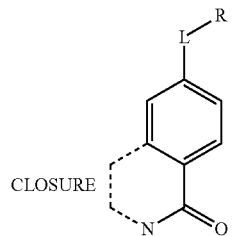

(I)

or a tautomer, stereoisomer or a pharmaceutically acceptable salt thereof, wherein:

the CLOSURE structure is absent and is replaced by a hydrogen atom on the phenyl ring and $H_2$ on the nitrogen atom of Formula(I);

L represents a linker of 1 or 2 linking atom(s) in a linear or in a branched conformation, said atom(s) being selected from the group consisting of: C, O, N or S, wherein at least one of the linking atoms is oxygen (O);

R is a saturated or unsaturated cycloalkyl or an unsaturated heterocyclic ring system consisting of 1 heterocyclic ring, wherein said cycloalkyl or heterocyclic ring system optionally comprises at least one substituent selected from the group consisting of: H, F, Cl, Br, I, $C_{1-3}$ alkyl, halogen-substituted $C_{1-3}$ alkyl, $C_{1-3}$ alkoxy, halogen-substituted $C_{1-3}$ alkoxy, —CN, —OH, —COOH, —$CONH_2$ and —$NO_2$;

with a sample suspected or known to comprise mARTDs in order to inhibit activity of the mARTDs in the sample.

11. The method according to claim 10, wherein said method comprises a further step of contacting said compound with a control sample comprising a mono ADP-ribosyltransferase (mARTD).

12. The method according to claim 10, the compound having a formula

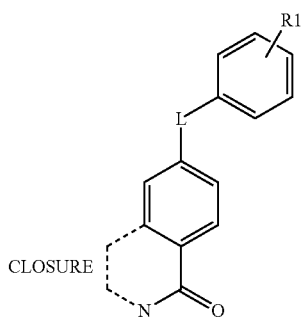

(II)

wherein:

the CLOSURE structure is absent, and wherein the CLOSURE structure of Formula (I) is replaced by a hydrogen atom on the phenyl ring and $H_2$ on the nitrogen atom;

L represents a linker of 1 or 2 linking atom(s) in a linear or in a branched conformation, said atom(s) being selected from the group consisting of: C, O, N or S, wherein at least one of the linking atoms is oxygen (O);

wherein R1 is optionally present on a 2, 3 or 4 position of the phenyl group and represents a member selected from the group consisting of: H, F, Cl, Br, I, $C_{1-3}$ alkyl, halogen-substituted $C_{1-3}$ alkyl, $C_{1-3}$ alkoxy, halogen-substituted $C_{1-3}$ alkoxy, —CN, —OH, —COOH, —$CONH_2$ and —$NO_2$.

13. The method according to claim 10, wherein linker L is selected from the group consisting of: O and O—$CH_2$.

14. The method according to claim 12, wherein said compound is 4,4'-oxydibenzamide having the formula:

(III)

15. The method according to claim 10, the compound having the formula

(IV)

wherein the CLOSURE is absent and is replaced by —H on a carbon atom of the phenyl group and by $H_2$ on the nitrogen atom, and wherein R1 is optionally present on a 2, 3 or 4 position of the phenyl group and represents a member selected from the group consisting of: H, F, Cl, Br, I, $C_{1-3}$ alkyl, halogen-substituted $C_{1-3}$ alkyl, $C_{1-3}$ alkoxy, halogen-substituted $C_{1-3}$ alkoxy, —CN, —OH, —COOH, —$CONH_2$ and —$NO_2$, and wherein the linker L of Formula (I) contains linking atoms A and B, and wherein A and B together represent linkers selected from O—$CH_2$, $CH_2$—O, O—C(═O) or C(═O)—O.

16. The method according to claim 15, the compound having the formula

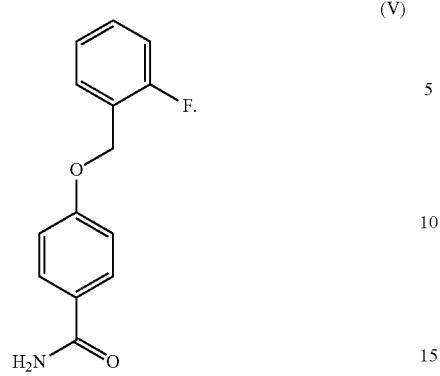
(V)
* * * * *